United States Patent
Motherway et al.

(10) Patent No.: US 9,763,676 B2
(45) Date of Patent: Sep. 19, 2017

(54) SURGICAL BLADE FOR USE WITH AN ACETABULAR CUP REMOVER TO REMOVE BONE AROUND AN ACETABULAR CUP

(71) Applicant: Stryker Ireland, Ltd., Kalamazoo, MI (US)

(72) Inventors: Julie Motherway, County Cork (IE); Kevin O'Flynn, County Dublin (IE)

(73) Assignee: STRYKER IRELAND, LTD, Kalamazoo, MI (US)

( * ) Notice: Subject to any disclaimer, the term of this patent is extended or adjusted under 35 U.S.C. 154(b) by 0 days.

(21) Appl. No.: 14/969,712

(22) Filed: Dec. 15, 2015

(65) Prior Publication Data

US 2016/0100846 A1    Apr. 14, 2016

Related U.S. Application Data

(63) Continuation of application No. PCT/IB2014/001496, filed on Aug. 8, 2014.

(60) Provisional application No. 61/840,575, filed on Jun. 28, 2013.

(51) Int. Cl.
  *A61B 17/00* (2006.01)
  *A61B 17/16* (2006.01)
  *A61F 2/46* (2006.01)
  *A61B 17/14* (2006.01)

(52) U.S. Cl.
  CPC ........ *A61B 17/1666* (2013.01); *A61B 17/142* (2016.11); *A61F 2/4609* (2013.01); *A61F 2002/4619* (2013.01); *A61F 2002/4628* (2013.01); *A61F 2002/4629* (2013.01)

(58) Field of Classification Search
  CPC combination set(s) only.
  See application file for complete search history.

(56) References Cited

U.S. PATENT DOCUMENTS

| | | | |
|---|---|---|---|
| 5,830,215 A | 11/1998 | Incavo et al. | |
| 8,034,059 B2 | 10/2011 | Tulkis | |
| 2002/0116007 A1 | 8/2002 | Lewis | |
| 2006/0200165 A1* | 9/2006 | Tulkis | A61B 17/1666 606/99 |
| 2007/0123893 A1* | 5/2007 | O'Donoghue | A61B 17/142 606/82 |
| 2008/0195111 A1 | 8/2008 | Anderson | |

FOREIGN PATENT DOCUMENTS

WO    2014/133536 A1    9/2014

OTHER PUBLICATIONS

PCT "International Search Report and Written Opinion" for PCT/IB2014/001496, dated Dec. 2014.

* cited by examiner

Primary Examiner — Sameh Boles

(57) ABSTRACT

A surgical blade (180) designed for use with an acetabular cup remover (30). The blade includes a body (182) from which teeth (190) extend distally forward. The body and teeth are disposed around the section of a sphere. On each side of the longitudinal axis of the blade body there is an outer tooth and at least two inner teeth. The teeth are further shaped so that one each side of the longitudinal axis through the blade body there are at least two adjacent inner teeth that have rake surfaces located along axes that, extending from the outer surface of the blade body to the inner surface of the blade body, do not intersect.

20 Claims, 16 Drawing Sheets

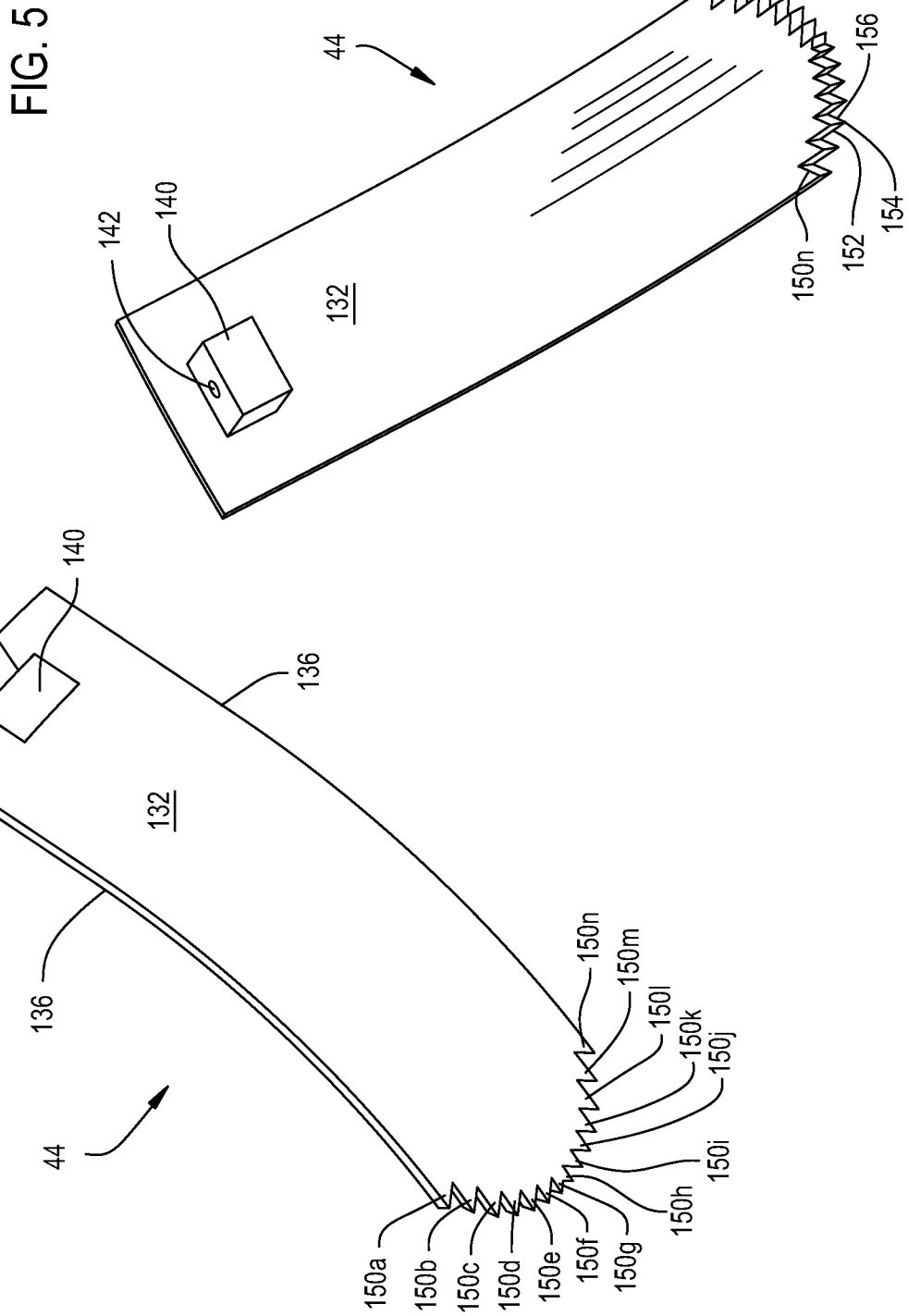

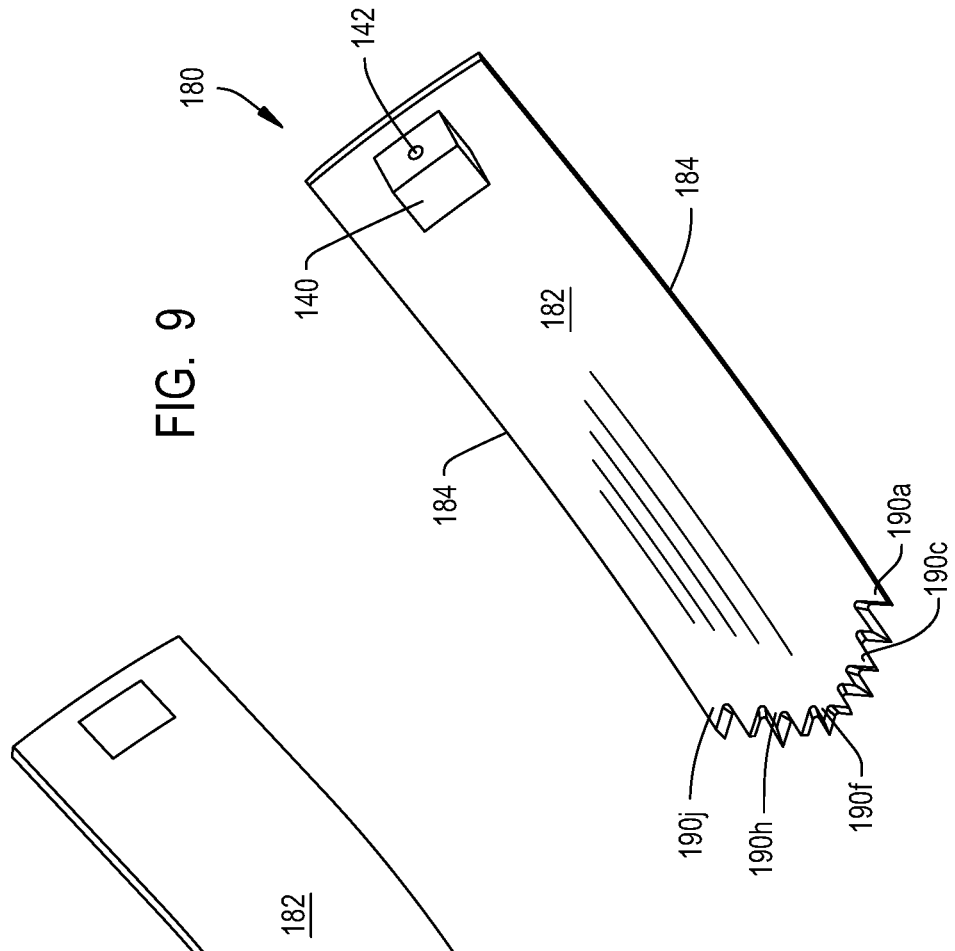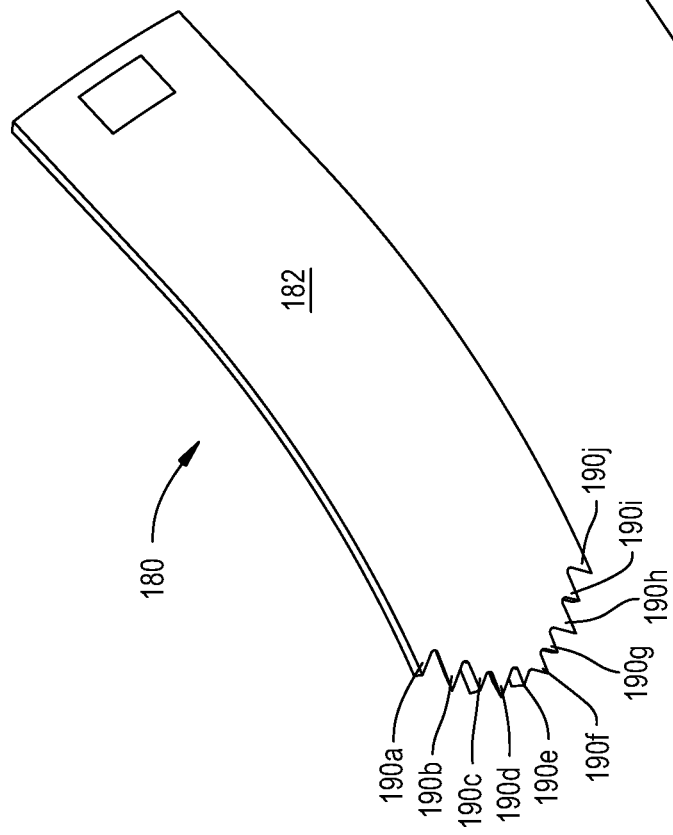

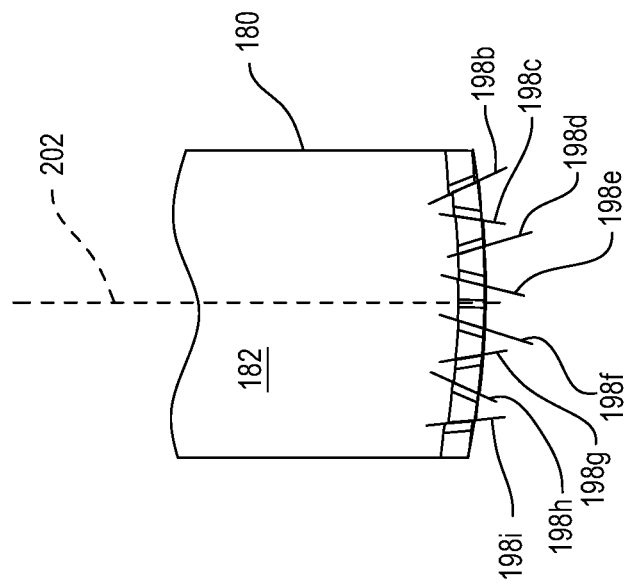
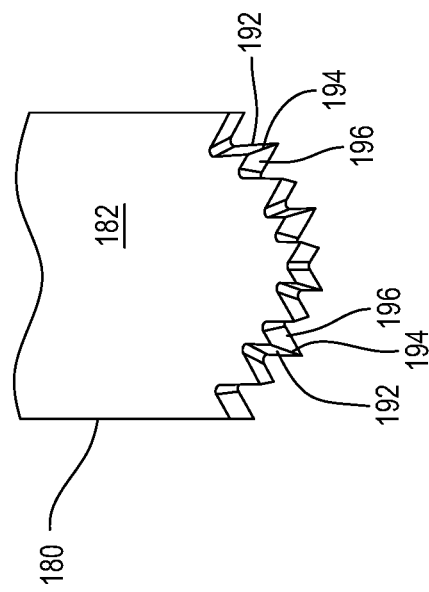

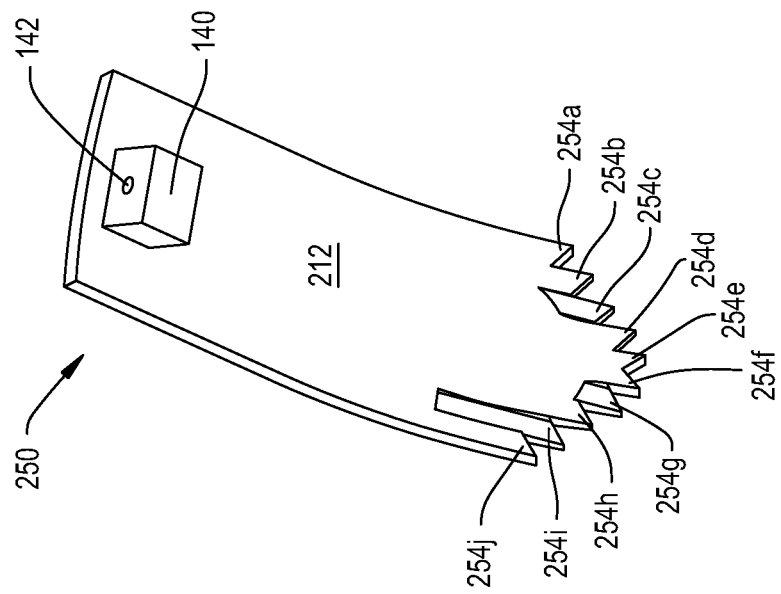
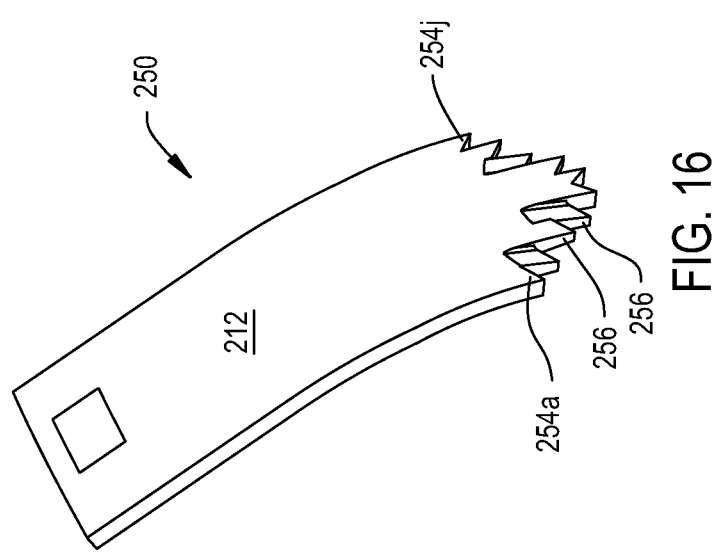

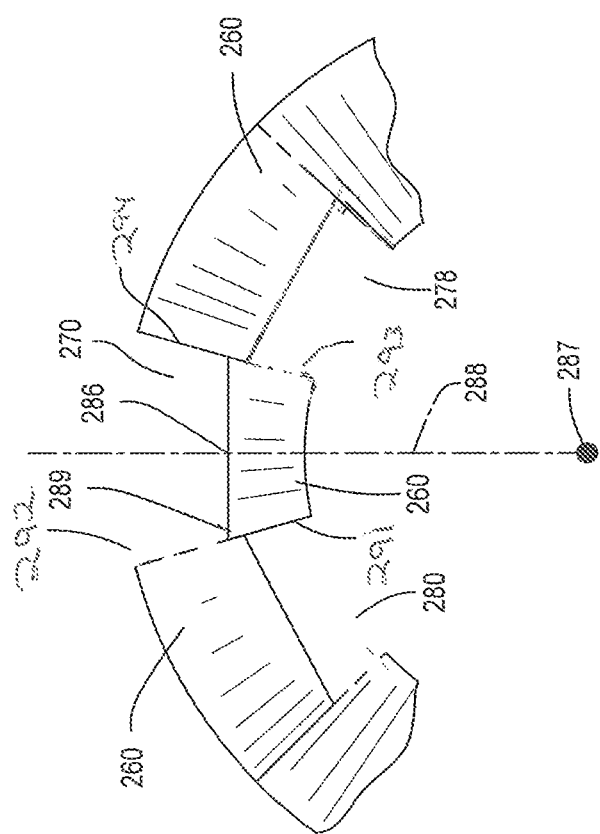

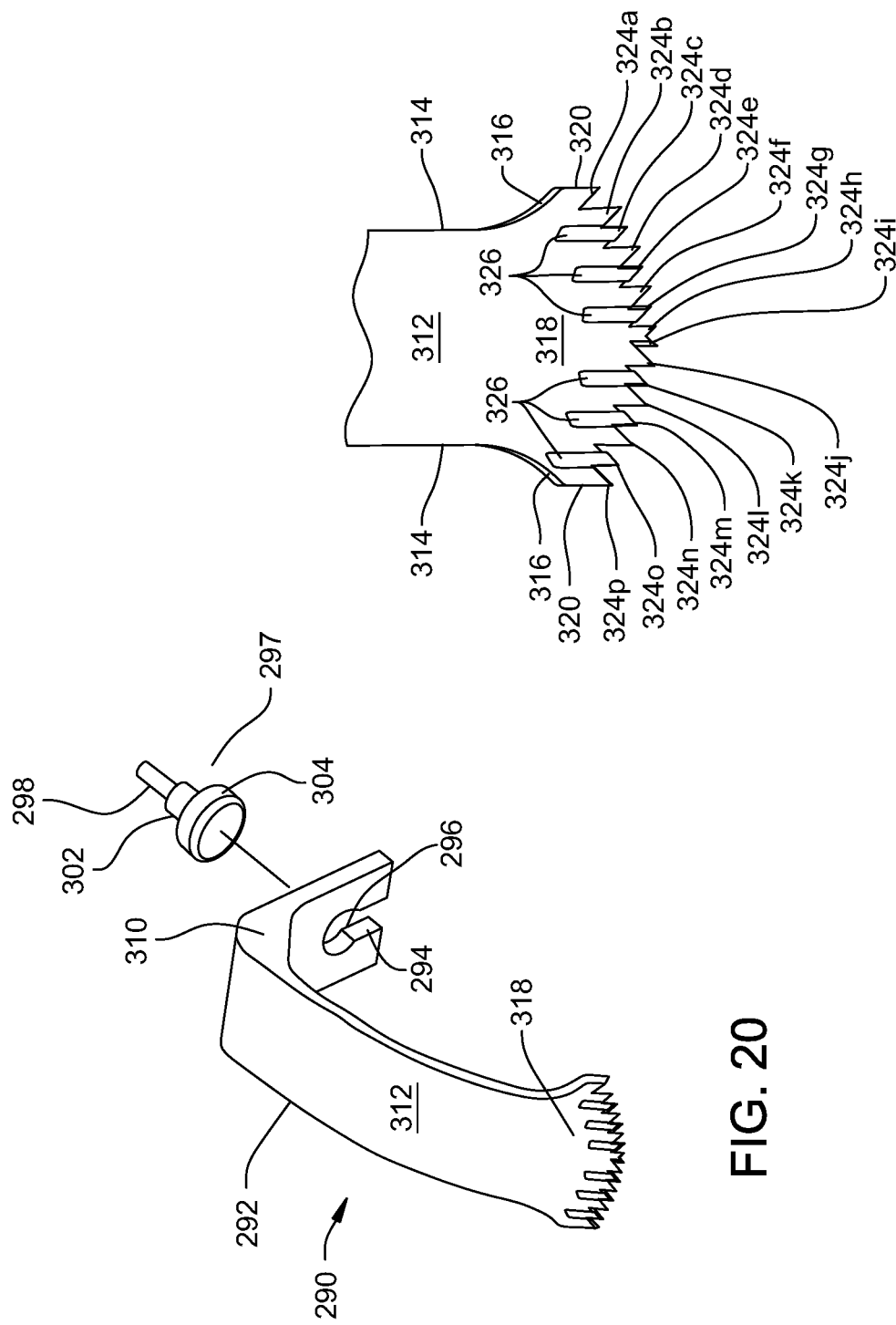

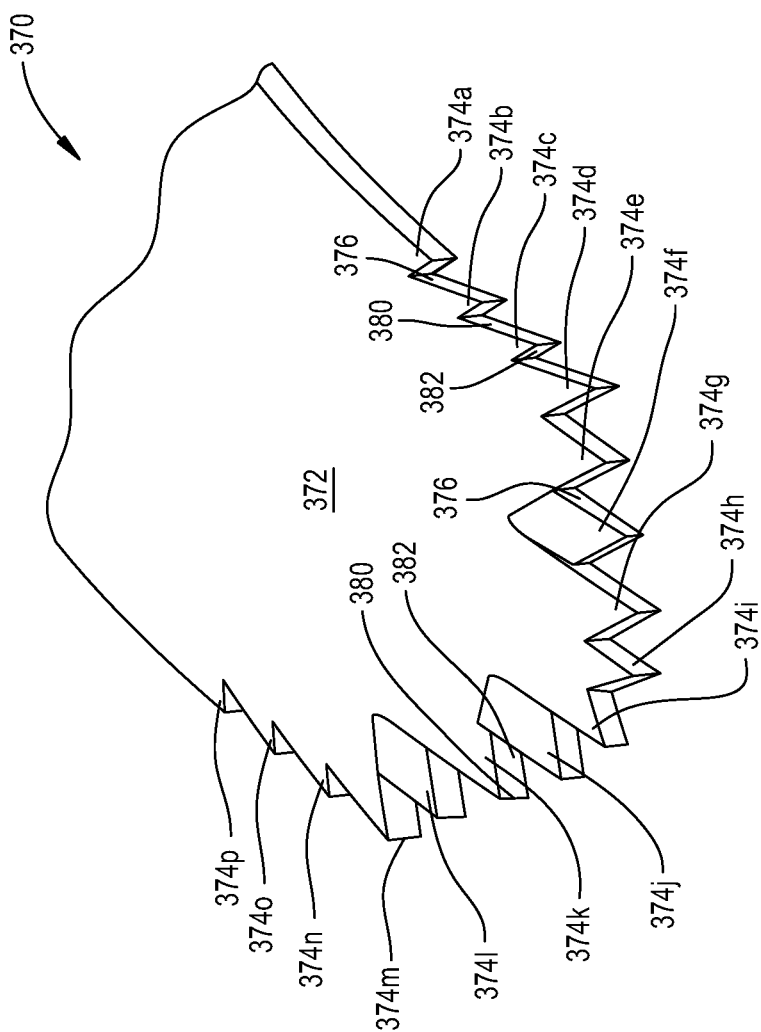

SURGICAL BLADE FOR USE WITH AN ACETABULAR CUP REMOVER TO REMOVE BONE AROUND AN ACETABULAR CUP

FIELD OF THE INVENTION

This invention relates to an acetabular cup remover. The acetabular cup remover of this invention has a blade that is especially designed to remove bone to which the cup is attached.

BACKGROUND OF THE INVENTION

One area of the body which is prone to chronic pain and degeneration of normal function is the hip joint. Whether caused by disease or injury, a portion of the population suffers from ailments relating to the hip. An often utilized solution to problems pertaining to the hip joint is total hip replacement ("THR") surgery. Generally, THR surgery consists of the replacement of the existing ball and socket of the hip joint with prosthetic replacements. The head of the femur, the ball, is typically removed and replaced with a femoral component made of biocompatible material, which approximately replicates the shape of the original bone. The acetabulum, the socket, is typically reamed and fitted with a prosthetic acetabular cup component that corresponds and cooperates with the femoral component. This prosthetic acetabular cup component often times includes an outer shell constructed of a synthetic material. Typically this shell is in the form of a hollowed out semi-sphere. An insert constructed of plastic, ceramic or metal, is received within the outer shell. The cup may be anchored in the bone through the use of cement. Some cups are press fit in place. Still other cups are held in place by screws or fastening fins or posts integral with the cup itself. A combination of these fastening methods may be employed. Sometimes, owing to the shape of the outer shell and/or the application of compounds that enhance bone growth, the outer shell is designed to foster the growth of bone adjacent the shell. This new bone anchors the cup to the rest of the hip. Total hip replacement surgery has often proven successful in relieving many problems associated with the hip joint.

Total hip replacement surgery is often successful. Nevertheless, it is sometimes necessary to perform the same surgery on the same hip. For example, this may be necessary in situations in which wear or infection degrade the performance of the installed cup and femoral head. This sub-set of total hip replacement surgery is sometimes called revision surgery. In revision surgeries, it may be necessary to remove the acetabular component previously implanted in the acetabulum. As mentioned above, these components may have been cemented in place or otherwise held by bone or fibrous tissue that may have grown in and around the component. The removal of a cup requires the cutting or chipping away of the bone and cement immediately adjacent the cup.

The Inventors' Assignee's U.S. Pat. No. 8,034,059, ACETABULAR SHELL REMOVAL INSTRUMENT, issued 11 Oct. 2011, the contents of which are explicitly incorporated herein by reference, discloses a surgical tool, acetabular cup remover, designed to perform a revision process. As its name implies, this tool is designed to remove an implanted acetabular cup. This tool includes a head that is dimensioned to seat in and rotate in the implanted cup. Plural shafts extend away from this head. A blade is pivotally mounted to one of these shafts. The blade curves forward such that the blade curves around the head. One of the shafts moves longitudinally relative to the head. The blade is connected to this first shaft to pivot as a function of the longitudinal movement of the shaft. A second shaft is rigidly connected to the head. The blade is connected to this second shaft. Axial rotation of this second shaft results in a rotational movement of the blade around an arc. The second shaft is connected to a power tool that oscillates the shaft.

This tool is used by seating the head in the cup that is to be removed. The first shaft is pressed downwardly. This results in the pivoting of the blade against the bone in adjacent the cup. The power tool is actuated. Thus simultaneously the blade is pressed against bone and oscillated in an arc around the cup. The blade shears the bone adjacent the cup. The tool is indexed and the blade pivoted so that the blade forms a cut that extends circumferentially around the portion of the cup embedded in the bone. The formation of this cut separates the cup from the bone in which the cup is embedded. This facilitates cup removal. A new cup is then installed.

The Applicant's PCT App. No. PCT/US2013/028535, ACETABULAR CUP REMOVER WITH INDEXING ASSEMBLY FOR ROTATING THE REMOVAL BLADE AROUND THE CUP, published as WO 2014/133536/US Pat. Pub. No. 2015/0359641 A1, the contents of which are also incorporated herein by reference, disclose a cup remover that has a mechanism for rotating the shaft to which the blade is pivotally attached. This feature reduces the ergonomic strain to which the practitioner is exposed when removing the cup.

The above discussed assemblies are useful for rotating the cup remover blade so the blade moves distally forward and indexing the blade so the blade moves circumferentially around the cup. However to date, the blades designed for use with these tools have not proven to be particularly efficient devices for cutting bone away from the cup to which the tool is fitted.

SUMMARY OF THE INVENTION

This invention is directed to an acetabular cup remover with a blade designed to, when oscillated adjacent the cup to which the blade is applied, efficiently shear away bone that surrounds the cup. The blade of this invention typically includes an elongated body. The body is curved both along the longitudinal and lateral axis of the body. These curves define a slice section of surface of a sphere. The blade is thus shaped so the inner surface of the body has a diameter slightly larger than the diameter of cup against which the body is applied. Teeth extend outwardly from the distal end of the blade body. Each tooth has a rake surface and a clearance surface. These surfaces extend proximally rearward from a common edge, the cutting edge, of the tooth. Since the teeth are extensions of the blade body, the teeth lie on the surface of the sphere defined by the blade body.

Some versions of the cup remover of this invention include a blade with teeth that are shaped so that essentially the whole of their cutting edges press against the bone that surrounds the acetabular cup intended for removal. Some embodiments of this version of the invention are constructed so that rake surfaces of many, if not all, of the teeth are along planes defined by axes parallel to the longitudinal center plane of the blade. These planes are also defined by axes that extend through a virtual center. This center is the center of the sphere of the acetabular cup the cup remover is employed to remove.

Some versions of this invention include a blade with teeth with rake surfaces designed to force bone chips cut by the blade away from the blade cutting edge. Some embodiments of this version of the invention include teeth with rake surfaces that extend out at an angle relative to a radial plane. Here the radial plane is the plane that is defined by a first axis that extends from the virtual center to the tip of the tooth and a second axis that extends from the tip of the tooth parallel to the longitudinal center plane of the blade.

It is a further feature of some versions of this invention that the blade includes one or more proximally extending grooves. These grooves function as channels through which the bone chips cut by the blade are able to flow away from the cutting edge. In some embodiments of the invention, each groove has a width that extends across the whole of the tooth in which the groove is formed. In still other embodiments of the invention, the groove has a width less than the width of the tooth with which the groove is associated. Often, in these versions of the invention, the groove is further located to be spaced away from the cutting edge of the tooth with which the grove is associated.

Some blades of this invention are firmed with a wide width distal end. Specifically, the distal ends of these blades are wider than the blade body from which these ends extend. The blades of this invention have teeth that extend outwardly from the portions of the blade located lateral to the sides of the blade body.

Other blades of this invention are formed with cutting edges that extend along the longitudinal sides of the blade. These cutting edges cut soft tissue away from acetabular cup against which the blade is applied.

BRIEF DESCRIPTION OF THE DRAWINGS

The invention is pointed out with particularity in the claims. The above and further features and benefits of this invention are understood from the following detailed description taken in conjunction with the accompanying drawings in which:

FIG. 4 is a perspective view of the outer surface of a blade of this invention;

FIG. 5 is a perspective view of the inner surface of the blade of FIG. 4;

FIG. 8 is a perspective view of the outer surface of a second blade of this invention;

FIG. 9 is a perspective view of the inner surface of the blade of FIG. 8;

FIG. 10 is an enlarged plan view of the inner surface of the distal portion of the blade of FIG. 8;

FIG. 11 is a plan view of the teeth and inner surface the blade of FIG. 8;

FIG. 16 is a perspective view of the outer surface a fourth blade of this invention;

FIG. 17 is a perspective view of the inner surface of the blade of FIG. 16;

FIG. 18A is a plan view of the distal end of the blade of FIG. 18;

FIG. 20 is a perspective view of the outer surface of a fifth blade of this invention;

FIG. 21 is a plane view of the blade of FIG. 20;

FIG. 24 is a perspective view of a seventh blade of this invention;

DETAILED DESCRIPTION

Figure 1:
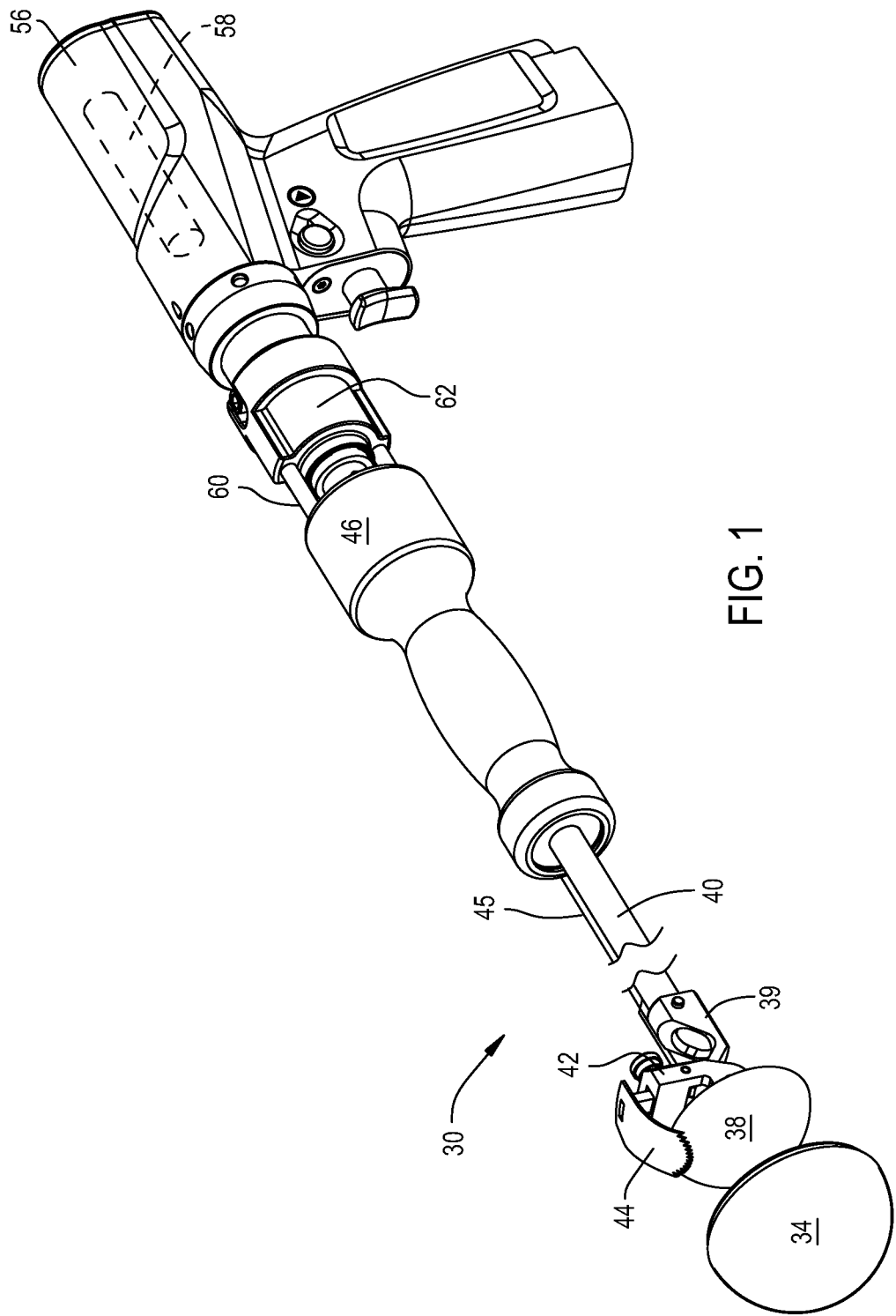
FIG. 1 is a perspective view of the acetabular cup remover with the blade of this invention.

FIG. 1 illustrates a surgical tool, acetabular cup remover 30 with a blade 44, of this invention and the relation of the tool to an acetabular cup 34. The cup 34 is often in the form of a hollow semi-spherical structure typically formed of metal. The outer surface of the cup 34 is embedded in bone of the hip. Sometimes cup 34 is actually embedded in cement. The inner surface of the cup defines a socket. This socket is shaped to receive the ball of a femoral stem. While not illustrated, a liner, often in the form of a hollow semi-spherical structure, may be seated against the inner surface of the cup 34. A liner, when present, defines the socket space that receives the femoral ball.

The cup remover 30 includes a head 38. Head 38 is the portion of the cup remover 30 that is seated in the cup 34. A shaft 40 extends proximally from the head 38. ("Proximally," it is understood means towards the surgeon using the cup remover 30, away from the cup 34. "Distally" means away from the surgeon, towards the cup 34.) The blade 44 is pivotally attached to shaft 40 a short distance proximally rearward from the head. Blade 44 has an arcuate profile and is positioned so as to curve distally forward and around the head 38. More particularly, the blade 44 is shaped so that when the head 38 is seated in the cup 34 the blade, when pivoted distally forward, advances around the outer surface of the cup.

A hinge 42 pivotally connects the blade 44 to shaft 40. Hinge 42 pivots the blade around a pivot axis so as to advance and retract the blade relative to the distal end of head 38. This pivot axis is understood to be in a static location relative to shaft 40. A handle 46 is slidably disposed over shaft 40. The handle 46 connected to hinge 42 by a rod 45 (only partially seen in FIG. 1) to pivot the hinge. Hinge 42, rod 45 and handle 46 collectively are the blade pivoting assembly.

Cup remover 30 is actuated by a power tool, referred to as a driver 56. Driver 56 includes a motor 58, depicted as a phantom cylinder. A coupling assembly 60 releasably connects the tool 30, namely the shaft 40 and handle 46, to driver 56. A transmission assembly, depicted by ring 62, converts the rotational movement of the shaft integral with the motor 58 into an oscillatory motion (motor shaft not illustrated). This motion is transmitted by the coupling assembly to the cup remover shaft 40 as oscillatory motion. The oscillation of shaft 40 results in a like oscillation of blade 44. The coupling assembly 60 and driver transmission 62 collectively form an indexing assembly. This indexing assembly allows the surgeon, by rotating handle 46, to set the rotational orientation of the cup remover shaft 40 around an axis that extends longitudinally through the shaft 40. The indexing of shaft 40 results in a like setting of the rotational orientation of blade 44 relative to cup 34. The structure of the coupling assembly 60 and the driver transmission 62 are not part of the present invention.

Figure 3:
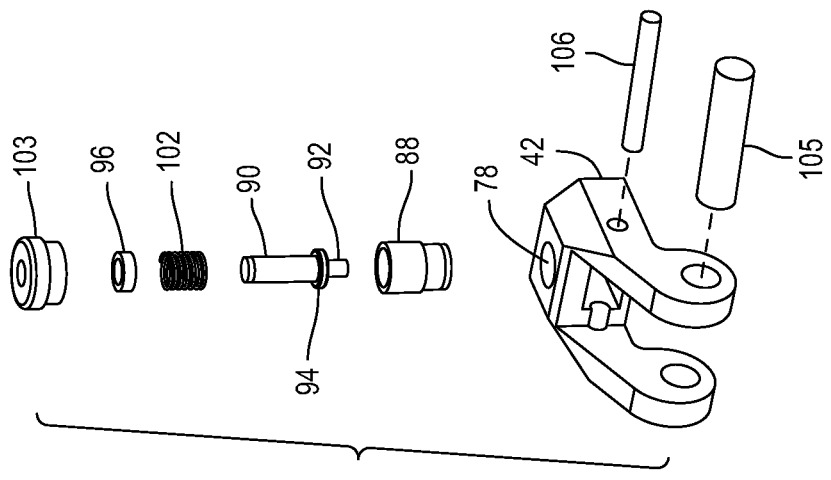
FIG. 3 is an exploded view of the components mounted to the hinge to facilitate the removable coupling of the blade to the hinge.
Figure 2:
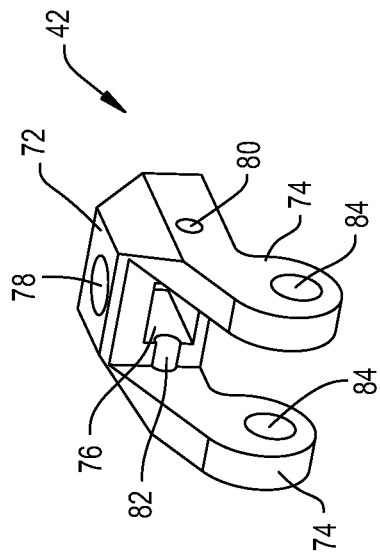
FIG. 2 is a perspective view of the hinge of the acetabular cup remover.

The hinge 42, seen best in FIGS. 2 and 3, includes a base 72 that is approximately rectangular in shape. Base 72 includes top located side surfaces that are inwardly tapered toward each other (surfaces not identified). Two parallel legs 74 project outwardly from one end of the base 72. Hinge 42 is shaped so that the legs 74 can slip fit over the opposed parallel flat surfaces of the shaft. Each leg 74 is formed so as to have a rounded free end (not identified).

The hinge 42 is formed so that a rectangular slot 76 extends through base 72. The longitudinal axis of slot 76 is parallel to the longitudinal axes of legs 74. Slot 76 is dimensioned to receive a below discussed tab 140 integral with the blade 44. An opening 78 extends through the top portion of hinge base 72. Opening 78 extends to slot 76. Coaxial openings 80 (one shown) extend through the opposed sides of the hinge 42 where the legs 74 extend from the base 72. Each opening 80 partially intersects the base 72. The face of the base 72 from which legs 74 extend adjacent is formed with two grooves 82 (one shown). Each groove 82 has a radius of curvature equal to the radius of the openings 80 and has a curve that is centered on the common axes through openings 80. Each leg 74 is formed with a through hole 84. Leg through holes 84 are coaxial.

The assembly that removably holds blade 44 to hinge 42, seen in FIG. 3, includes a sleeve like bushing 88. Bushing 88 is press fit in hinge opening 78. A lock pin 90 is disposed in bushing 88 to move up and down within the bushing. Lock pin 90 has a tip 92 designed to seat in bore 142 integral with blade 44 (FIG. 5). Above the tip 92 the lock pin 90 has a lip 94 that protrudes radially outwardly and circumferentially around the main body of the tip 92. A ring shaped retainer 96 is press fit into the end of bushing 88 spaced from the hinge 42. The components are further dimensioned so that the end of the lock pin 90 opposite tip 92 protrudes above retainer 96.

A helical spring 102 is disposed around the main body of the lock pin 90. Spring 102 extends between the static inner surface of retainer 96 and lip 94 integral with lock pin 90. The spring 102 places a force on the lock pin 90 that tends to hold the pin tip 92 in hinge slot 76. The end of the pin 90 opposite the tip 92, the section that extends above retainer 96, is attached to a button 103. In the absence of another force, spring 102 holds button 103 over bushing 88. This coupling assembly is moved from the run state to the load state by pulling on button 103. This manual force overcomes the force spring 102 applies to the pin 90 so as to hold tip 92 in the hinge slot 76.

Upon assembly of the cup remover 30, hinge 42 is positioned so that each leg through hole 84 is adjacent a separate one of the openings in the shaft 40 (openings not identified). In some versions of this invention, these openings are in a front end component a coupler 39, located between head 38 and shaft 40 that holds the head to the shaft. A pin 105 extends through hinge holes 84 and a through bore in the coupler to pivotally hold the hinge 42 to coupler 39. A pin 106 is seated in openings 80 and grooves 82. Pin 106 limits the extent to which blade tab 140 can be inserted in slot 76.

Rod 45 connects the handle 46 to hinge 42. The rod 45 may include an actuator, not identified that is the component of the rod actually connected to the hinge 42. The rod 45 and associated actuator are configured to, upon the linear displacement of the handle 46 up and down the shaft 40, pivot hinge 42 around the axis through leg openings 84. The exact structure of the components that pivot the hinge is not part of the present invention.

Blade 44, as now described by reference to FIGS. 4-7, includes an elongated body 132. Body 132 has a proximal edge 134 from which two parallel side surfaces 136 extend. A rectangular opening 138 is formed in the proximal portion of the body so as to be located forward of proximal edge 134. Blade tab 140 is welded or otherwise secured in body opening 138. Tab 140 extends inwardly from the inner surface of body 132 towards shaft 40. The tab 140 is shaped to have a closed end bore 142 the opening of which is seen in FIG. 5. Bore 142 extends inwardly from the proximally directed surface of tab 140.

Blade body 132, at least the portion of the blade located distal to tab 140, is formed so that both the longitudinal (the proximal-to-distal) axis and the lateral axis (the side-to-side) axis) are both curved. More specifically, the blade body is formed so that along the inner surface of the body, the body has a common radius of curvature along these axes that is typically no more than 4 mm greater than the radius of the sphere defined by the acetabular cup 34 remover 30 is employed to remove. In many versions of the invention, the inner surface of blade body 132 has a common radius of curvature along these axes that is less than 2 mm greater than that the acetabular cup 34. Blade body 132 is further formed so that the medial portion of the distal end extends further distally than the opposed sides of the body. Proximal to the medial portion, the opposed faces of the blade body taper proximally the adjacent body side surfaces 136.

Teeth 150 extend distally forward away from the distal end of body 132. Since the teeth 150 are extensions of the blade body the teeth 150, as well as the other below-described teeth lie on the longitudinal and lateral radii of curvature of the blade body. Each tooth 150 has a rake surface 152 and a clearance surface 156. The rake surface 152 is the tooth surface that, when the tooth is moved against material to be cut, is the surface that faces the material to be cut. The clearance surface 156 is the surface that, as the tooth is moved against material to be cut, faces away from the material to be cut. The rake surface 152 and clearance surface 156 meet an edge 154, which is the cutting edge of the tooth 150. The clearance surfaces 156 of teeth 150a-150f and 150i-150n emerge from the blade body from a line along which the rake surface of the adjacent tooth emerges. The rake surfaces 152 of the outer teeth, teeth 150a and 150n, are extensions of the blade body surfaces defined by the blade body side surfaces 136. Thus, teeth 150 of the blade of this invention do not project laterally outwardly from the blade side surfaces 136. Blade 44 is further formed so that the two teeth closest to the opposed sides of the body longitudinal axis, teeth 150g and 150h, are shaped so that the clearance surfaces 156 of these teeth emerge from a common line that is perpendicular to the longitudinal axis of the blade body 132.

Figure 7:
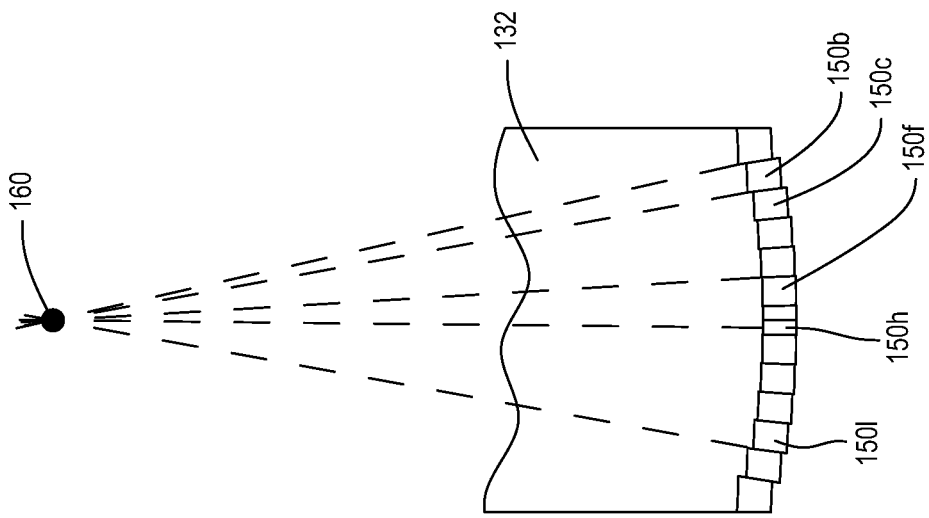
FIG. 7 is a plan view of the teeth of the blade of FIG. 4.
Figure 6:
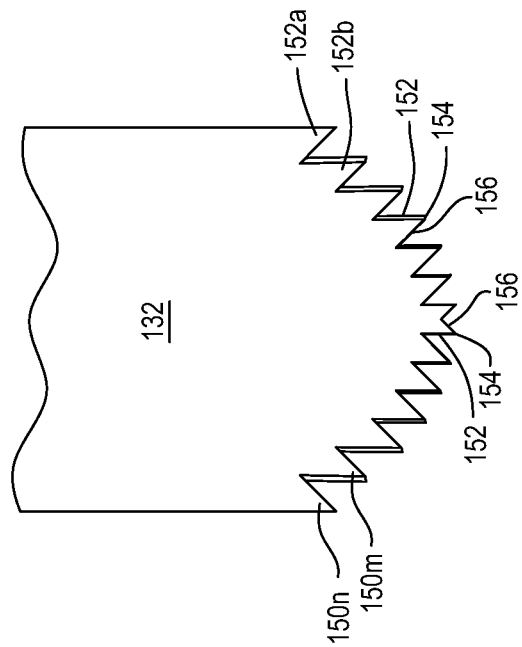
FIG. 6 is a plan view of the inner surface of the blade of FIG. 4.

The rake surfaces 152 of the outer two teeth, teeth 150a and 150n, are in parallel planes. The rake surfaces of the inner teeth, tooth 150b through 150m, lie in planes that are not parallel. Each of the rakes surfaces 152 of these teeth 150b through 150m lies in a plane defined by two axes. The first axis of each of these planes is an axis parallel to the longitudinal axis of the blade body 132. The second axis of each of these planes intersects the first axis and intersects the center of the sphere defined by the common radius of longitudinal and lateral axes of the blade body. When the blade 44 is mounted to an acetabular cup remover 30 this center is thus also the cup remover head 38. This center is also therefore the center of the acetabular cup 34 against which blade 44 is to be applied. This is seen in FIG. 7 where dashed lines that represent the extensions of the cutting edges 154 of teeth 150b through 150m are shown to intersect at a common point 160. These dashed lines are also extensions of the second axes that define the planes of rake surfaces of teeth 150b, 150c, 150f, 150h and 150l. To minimize drawing complexity, the extension lines from the remaining teeth are not shown.

Cup remover 30 of this invention is prepared for use by first fitting the blade 44 to hinge 42. This is accomplished by pulling up on button 103. The manual force on applied to the button overcomes the force of spring 102 that holds pin tip 92 in hinge slot 76. Once the pin tip 92 is retracted away from the hinge slot 76, blade 42 is mounted to the hinge by seating the blade tab 140 in hinge slot 76. Once the blade tab bore 142 is in registration with the pin 90, button 92 is released. The force spring 102 applies to lock pin 90 holds the pin tip 92 in blade tab bore 142. The blade is thus removably coupled to the hinge 42.

The cup remover 30 is then coupled to driver 56. Cup remover 30 is then positioned so that the remover head 38 is seated in the center void of the acetabular cup 34 the remover is intended to remove. If a liner is present, the liner is typically removed prior to the seating of the head 38 in the cup 34.

The actuation of the driver 56 results in the oscillation of the blade 44 back and forth. Owing to the orientation of the teeth, the rake surfaces are at a 0° rake angle relative to the surface of the bone to which the teeth are applied. Consequently, the whole of each cutting edge 154 is applied against the uncut bone adjacent the cup to which the blade is applied. Thus, during a sweep of the tooth, in comparison to a blade with rake surfaces that are not radial, the rake surfaces 152 of the blade of this invention more fully press against the bone or cement against which the surface is rotated. A benefit of the rake surfaces so pressing against the bone is that it results in a like relative large volume of bone is sheared away from the area around the acetabular cup 34.

FIGS. 8 to 11 illustrate a second blade 180 of this invention. Blade 180 has a body 182 substantially identical to blade body 132. Body 182 has opposed parallel side surfaces 184 the edges of which are called out in FIG. 9. Tab 140 protrudes from blade body 182.

Teeth 190 extend from the distal end of blade body 182. Each tooth 190 has a rake surface 192 and a clearance surface 196 (two of each surfaces identified). The rake and clearance surfaces of each tooth meet at the cutting edge 194 of the tooth (two cutting edges identified). Each rake surface 192 is seated in a plane the first axis of which is parallel to the longitudinal center plane of the blade body 182. The rakes surfaces 192 of the outermost teeth, teeth 190a and 190j, are coplanar to the side surfaces 184 of blade body 182 from which the teeth extend. The inner teeth, teeth 190b through 190i, are formed so that the first axes that defines the planes of the rake surfaces of these teeth are, like the first axes of rake surfaces 152, lines that are parallel to the longitudinal center plane of the blade body 182.

Teeth 190b through 190i are further formed so as their rake surfaces 192 of adjacent teeth are located on planes the second axes of which do not intersect at a common point. Instead, the rake surfaces 192 of teeth 190b through 190i are on planes the second axes of which are angled relative to lines that radiate outwardly from the center of the acetabular cup 34 with which a tool 30 with blade 180 is used. More particularly, it can be seen that rake surface 192 of tooth 190b is located on an axis represented by line 198b that, extending proximally, towards a plane that extends through the center of the sphere, the plane represented by line 202. Line 202 also represents the proximal to distal longitudinal center plane along the blade body 182. This center plane is understood to be perpendicular to the lateral axis across the blade body 182. This means that extending proximally rearward from the blade cutting edge 194, in a cross section plane perpendicular to the longitudinal center plane of the tooth 190b, the outer surface of the tooth has a longer width than the underlying inner surface of the tooth. Stated another way, the rake surface 192 of tooth 198b is located on axis that, extending from the opposed outer and inner surfaces of the tooth is directed towards the longitudinal center plane of blade body 182.

Tooth 190c, the tooth adjacent to tooth 190b that is located closer to the longitudinal center plane of the blade body, has a rake surface 192 that is located on an axis represented by line 198c. Line 198c, extending proximally extends away from the plane 202 that extends through the center of the sphere of sphere of cup 34. Thus extending distally from the cutting edge of tooth 190c in a cross section plane perpendicular to the longitudinal center plane of the tooth the inner surface of the tooth has a longer width across the tooth than the overlying width of the outer surface of the tooth. An alternative way to describe the second axis of rake surface 192 of tooth 196c is that this axis extending from the opposed outer and inner surfaces of the tooth, is directed away from the longitudinal center plane of the blade body 182.

Tooth 190d is the tooth adjacent tooth 190c that is located closer to the longitudinal center plane of blade body 182. Tooth 190d has a rake surface that, like the rake surface of tooth 190b, is located on an axis that, extending proximally extends towards the plane that intersects the center of the sphere. This means that the second axis of the rake surface 192 of tooth 190d, extending from the outer and inner surfaces of the tooth 190d, as represented by line 198d, is angled towards the longitudinal center plane of the blade body. Tooth 190e is the tooth on the right side of the blade of FIG. 11 that is closest to the longitudinal center plane of blade body 182. Tooth 190e has a rake surface with a taper, a second axis in the same orientation of the taper, the second axis, of tooth 190c.

The teeth 190f-190i on the left side of the longitudinal center plane of blade body 182 as seen in FIG. 11, have rake surfaces with tapers, second axes that are reverse of teeth with which they are symmetrically opposed relative to the longitudinal center plane. Thus, tooth 190f, which is the tooth symmetric with respect to tooth 190e has a rake surface located on an axis, represented by line 198f, that extends inwardly toward the blade body longitudinal center plane represented by line 202. Again it is understood each of these references are in the direction of the axes extending from the outer and inner surfaces of the teeth formed by the rake surfaces. Tooth 190g, the tooth symmetric with respect to tooth 190d, has a rake surface represented by line 198g, that extends outwardly relative to the blade body from the longitudinal center plane. Tooth 190h is the tooth that is symmetric with respect to tooth 190c. Thus, where tooth 190c has a rake surface located on an axis that extends outwardly, tooth 190h has a rake surface located on an inwardly extending axis, represented by line 198h. Teeth 190b and 190i are symmetric around the longitudinal center plane of blade body 182. Where tooth 190b has a rake surface that tapers inwardly towards the blade body longitudinal center plane, tooth 190i has a rake surface located on an axis represented by line 198i that extends outwardly from the blade body longitudinal center plane.

Figure 11A:
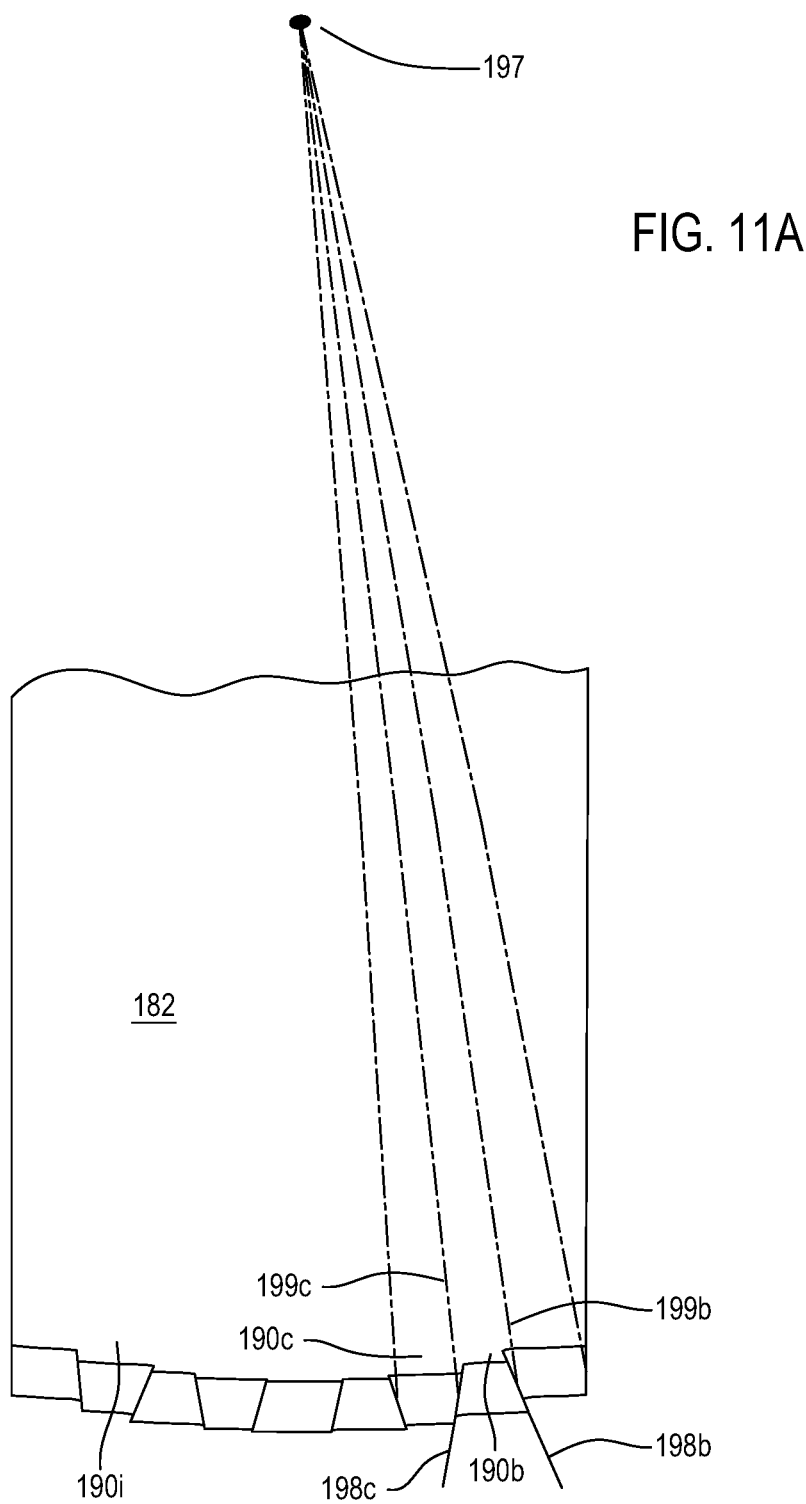
FIG. 11A is an enlarged plan view of blade teeth depicted in FIG. 11.
Figure 13:
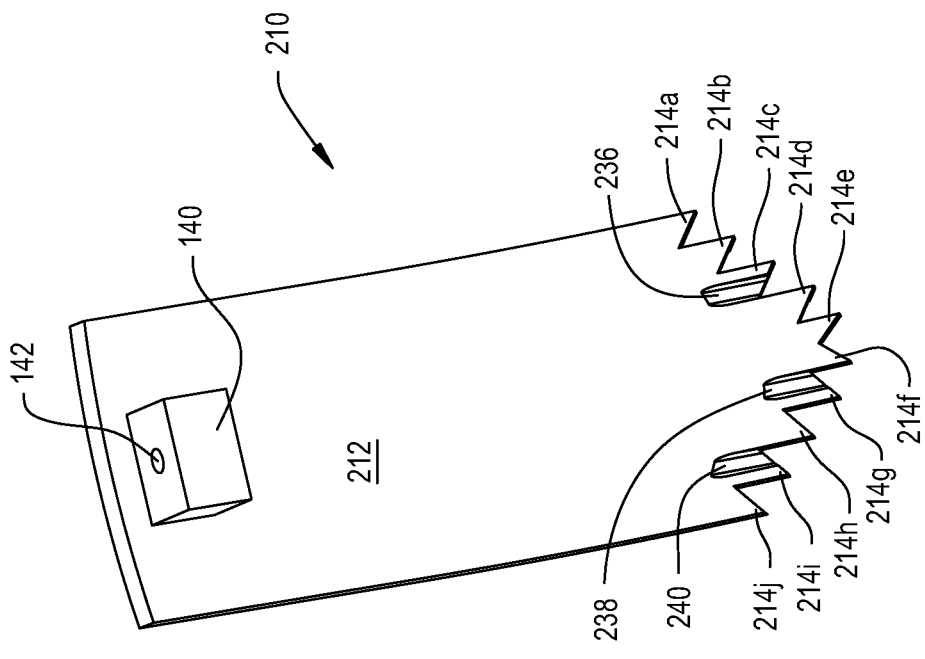
FIG. 13 is a perspective view of the inner surface of the blade of FIG. 12.

FIG. 11A provides a further understanding of this shear. In FIG. 11A, the axes defining the shear of teeth 190b and 190c are again represented by solid lines 198b and 198c. Dot and dashed lines, lines 199b and 199c, are the radial lines that extend from the virtual center of blade 180, point 197. This center is the center of the cup with which the blade is to be used. In a common plane radial line 199b intersects axis line 198b. The angle of this intersection is the shear angle. In many versions of the invention the shear angle, sometimes called the taper, is at angle of 30° or less, and often 20° or less. In the illustrated version of the invention, the shear angles of the adjacent rake surfaces 192 are equal.

Blade 180 is attached to tool 30 using the same method by which blade 44 is attached. Tool 30 is then prepared for use using the method previously described. The actuation of the driver 56 results in the oscillation of the blade 180. As the blade moves against the bone the cutting edge shears the bone. When the blade 180 as seen in FIG. 11 moves to the right, the cutting edges of teeth 190a through 190e shears the bone. Owing to the angle of rake surfaces of teeth 190b and 190d the debris adjacent these rake surfaces are directed towards the inner surface of the blade 180. This minimizes the build up of debris against the cutting edges of these teeth. At the same time, owing to the orientation of the rake surfaces 192 integral with teeth 190c and 190e, the debris adjacent these rake surfaces are forced towards the outer surface of the blade. When blade 180 as seen in FIG. 11 moves to the left, the cutting edges 192 of teeth 190f through 190j shear against bone. Owing to the orientation of the rake surfaces 192 integral with teeth 190f and 190h the debris adjacent these teeth are pushed toward the inner surface of the blade 180. Owing to the orientation of the rake surfaces 192 integral with teeth 190g and 190i, debris adjacent these teeth are pushed towards the outer surface of the blade 180. This forcing of the debris toward the inner and outer surfaces of the blade minimizes the accumulation of the debris against the teeth cutting edges. The minimization of debris accumulation results in a like reduction in which the presence of these debris reduces the efficiency of the bone (or cement) removal process.

Figure 12:
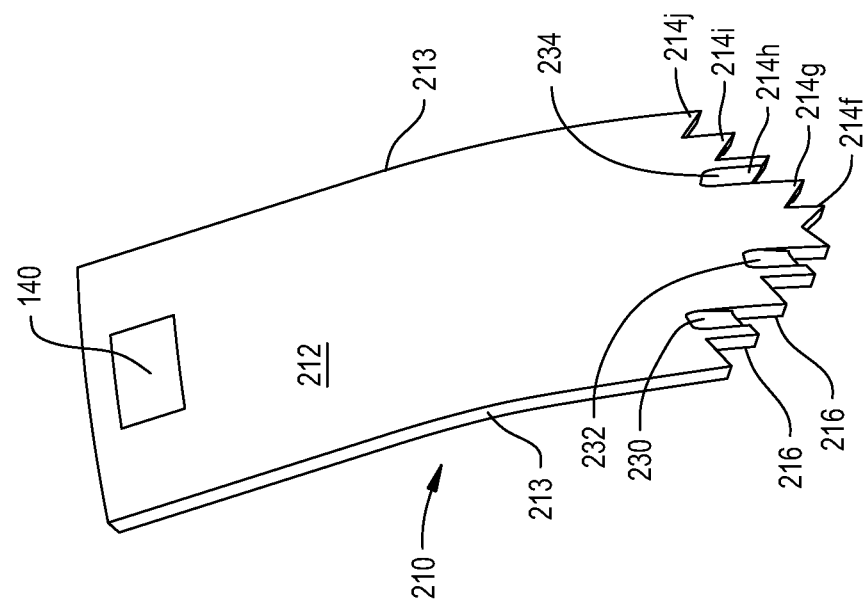
FIG. 12 is a perspective view of the outer surface a third blade of this invention.
Figure 15:
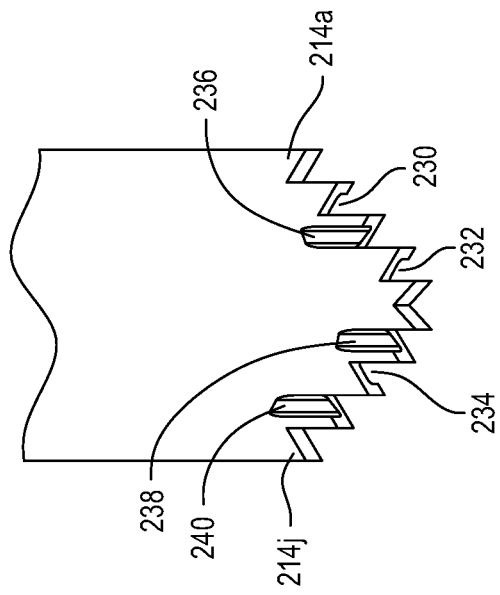
FIG. 15 is an enlarged view of the distal end of the blade of FIG. 12 wherein the inner surface and distal end face of the blade are seen in detail.

A third blade 210 that can be used as part of the cup remover 30 of this invention is now described by reference to FIGS. 12 through 15. In Blade 210 includes a body 212. Body 212 has the same basic shape as the previously described blade body 132. Body 212 has opposed side surfaces 213, at least the edges of which are seen in FIG. 12. Tab 140 protrudes outwardly from the inner surface of body 212.

Teeth 214, individually, tooth 214a through tooth 214j, project distally forward from the distal end of body 212.

Figure 14:
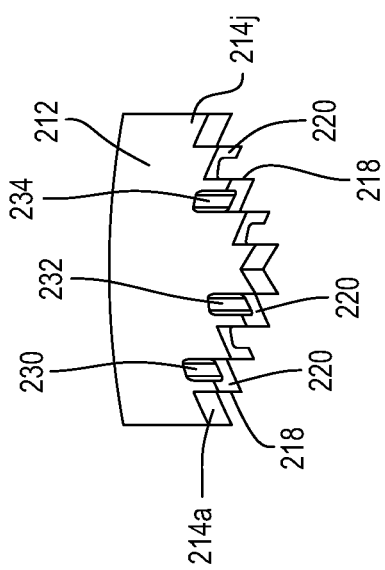
FIG. 14 is an enlarged view of the distal end of the blade of FIG. 12 wherein the outer surface and distal end face of the blade are seen in detail.
Figure 19:
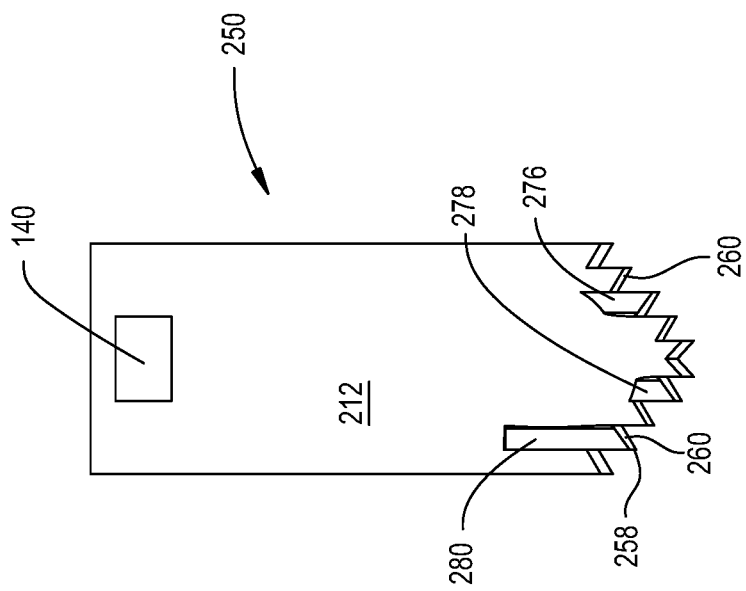
FIG. 19 is an enlarged view of the distal end of the blade of FIG. 16 wherein the inner surface and distal end face of the blade are seen in detail.
Figure 18:
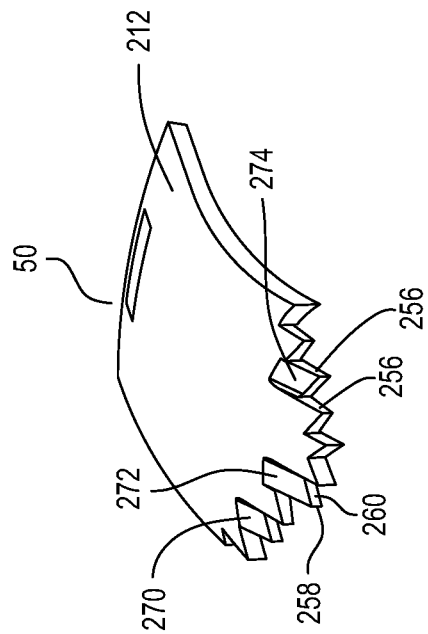
FIG. 18 is an enlarged view of the distal end of the blade of FIG. 16 wherein the outer surface and distal end face of the blade are seen in detail.

Each tooth 214 has a rake surface 216 (two identified in FIG. 12) and a clearance surface 220 (three identified in FIG. 14). The rake and clearance surfaces 216 and 220, respectively, of a tooth 214 extend proximally rearward from the cutting edge 218 of the tooth (two cutting edges identified in FIG. 14). In the depicted version of the invention the rake surfaces of the outermost teeth, teeth 214a and 214j, are each coplanar with the side surface 213 from which it extends distally forward. Teeth 214b through 214i have rake surfaces 216 similar to rake surfaces 152 of teeth 150b through 150m of blade 44. Each one of the rake surfaces 214 of teeth 214b through 214i is located on a first axis that is parallel to the longitudinal axis through the blade body and a second axis that radiates from the center of the sphere defined by the cup 34 with which remover 30 is used.

Blade 210 is further formed so as that grooves, sometimes referred to as channels or dubs, that extend proximally away from the clearance surfaces of some of the teeth. More particularly it can be seen that outer surface of blade body 212 is shaped to define three grooves 230, 232 and 234. Groove 230 extends proximally away from the outer edge of clearance surface 220 integral with tooth 214b. Groove 232 extends proximally away from the outer edge of the clearance surface 220 of tooth 214d. Groove 234 extends proximally away from the outer edge of clearance surface 220 of tooth 214h.

The blade 210 is further formed to have three grooves in the inner surface of the body that extend proximally away from the clearance surfaces of some of the teeth. Groove 236 extends proximally away from the inner edge of clearance surface 220 of tooth 214c. Groove 238 extends proximally away from the inner edge of clearance surface 220 of tooth 214g. Groove 240 extends proximally away from the inner edge of clearance surface 220 of tooth 214i.

Blade 210 is formed so that the depth of each groove 230-240 decreases as the groove extends proximally along the surface in which the groove is formed. The blade 210 is also shaped so that the width of the grooves 230-240 is less than the width of the clearance surfaces from which the grooves extends. Each groove is positioned to be spaced inwardly from the cutting edge 218 of the tooth with which the groove is formed. Thus, the presence of the grooves does not reduce the length of the associated cutting teeth. It should be further appreciated that relative to the inner and outer surfaces of the blade body 212, the grooves are interleaved. In other words between two adjacent grooves formed on the inner (or outer) surface a groove is formed on the outer (or inner) surface.

Cup remover 30 with blade 210 installed is prepared for use like the previously described blades 44 and 180. When the cup remover 30 with blade 210 is actuated, the cutting edges 218 shears against the bone adjacent the acetabular cup 34. This results in the removal of the bone. Grooves 230-240 function as conduits through which the debris formed by this bone removal process are able to flow away from the cutting edges 218 of the teeth 214. Since the debris have a conduit through which they are able to flow away from the cutting edges, the debris do not accumulate adjacent the cutting edges. This reduces the extent to which the build up of debris adjacent the cutting edges 218 of the teeth reduces the efficiency of the bone removal process.

In preferred versions of the invention, owing to how the grooves 230-240 are formed, the depths of the grooves are substantially identical. This ensures FIGS. 16-19 depict a fourth blade 250 of that can be incorporated into the cup remover 30 of this invention. Blade 250 has many of the same features of blade 210.

Accordingly, these features are not redescribed. Where blade 210 has teeth 214, rake surfaces 216, cutting edges 218 and clearance surfaces 220, blade 250 has teeth 254, rake surfaces 256, cutting edges 258 and clearance surfaces 260.

Blade 250 is formed with grooves 270-280 in the blade body 212. Grooves 270-274 are formed in the outer surface of the blade 250. More particularly, groove 270 extends over tooth 254*b*. Groove 272 extends over tooth 254*d*. Groove 274 extends over tooth 254*h*. Grooves 276-280 are formed in the inner surface of blade 250. More particularly, groove 276 extends over tooth 254*c*. Groove 278 extends over tooth 254*g*. Groove 280 extends over tooth 254*i*.

Grooves 270-280 are different from grooves 230-240 in that grooves 270-280 extend the whole of the widths of the clearance surfaces of the teeth 254 in which the grooves 270-280 are formed.

The recessed surfaces that define the bases of grooves 270-280 are each centered on two axes. These axes are seen in FIG. 18A wherein the surfaces of the blade that define groove 270 are depicted. One axis, the longitudinal axis, is an axis that is parallel to the longitudinal axis of the blade. This axis, which goes in and out of FIG. 18A, is represented by point 286. The second axis, the lateral axis, seen in FIG. 18A, is a line perpendicular to a radial line 288 that extends from the virtual center of the blade, point 287. This lateral axis, line 289, extends through the radial line 288 that intersects the longitudinal axis of the base of the groove. Generally the grooves are formed so that at no point along the length of the groove does the groove have a depth that is more than 50% of the overall thickness of the blade body. As mentioned above the lateral axis across each groove is a straight line. Therefore, as seen in FIG. 18A, the thickness of the portion of the blade below the groove is thinnest below the longitudinal axis of the groove.

FIG. 18A is a plan view of the distal end of the blade 250. Three clearance surfaces 260 are seen; the clearance surfaces 260 from which grooves 270, 278 and 280 extend proximally rearward. The cutting edge defined by the intersection of the clearance surface from which groove 278 extends and the complementary rake surface is depicted as solid line segment 291. Dashed line segment 292, which is collinear with line segment 291, represents the intersection of the rake surface of the tooth in which groove 280 is formed and the adjacent clearance surface from which groove 270 extends. In FIG. 18A, to the right of the cutting edge formed by the clearance surface over which groove 270 is the rake surface of tooth in which groove 278 is formed (rake surface not seen). Dashed line segment represents the corner from which the clearance surface over which groove 270 is formed extends forward from this next tooth over rake surface. Solid line 287, which is collinear with dashed line 293 represents the cutting edge formed by this next tooth over rake surface and the complementary clearance surface 280. This particular clearance surface is the clearance surface from which groove 278 extends.

In FIG. 18A the outer groove 270 is shown to have side walls that taper outwardly from the base of the groove. Inner grooves 278 and 280 are shown to be defined by sidewalls that taper inwardly from the bases of the grooves. This is for illustration only. In practice, as a result of the application of a grinding wheel to the blade to form the grooves, the grooves are typically formed with parallel sidewalls.

Cup remover 30 is prepared for use with blade 250 in the same general manner in which the cup remover 30 is previously described as being prepared for use.

When cup remover 30 including blade 250 is actuated, the cutting edges 258 of blade teeth 254 shears the bone that holds the acetabular cup 34 to the hip. Grooves 270-280 function as relatively large grooves through which the bone debris formed by this shearing process are able to flow away from the teeth cutting edges 258. This further reduces the presence of the efficiency reducing bone chips adjacent the blade cutting edges.

Grooves 270-280 extend across the complete widths of the clearance surfaces with which the grooves are associated. Therefore, the heights of the clearance surfaces 260 are reduced. By extension the lengths of the cutting edges 258 defined by the clearance surfaces 260 are also reduced. As mentioned above, in many versions of the invention, blade 250 is formed so that the presence of the groove does not reduce the height of the clearance surface, the length of the associated cutting edge by more than 50% in comparison to a tooth in which the groove is not present. This feature ensures that the presence of the grooves when placed on alternating sides of adjacent teeth do not result in the blade presenting to the bone a blade section in which there is no cutting edge is present.

FIGS. 20 and 21 depict a fifth blade, blade 290 of this invention. Blade 290 includes a single piece blade body 292. Blade body 292 has a foot 294 that is generally in the form of a rectangular plate. Foot 294 is formed to have an opening 296 that extends through the head. Opening 296 is a modified keyhole opening in that the opening has a central portion that is circular in shape and an extension that projects radially from the central portion, (opening portions not identified). The width of the extension is less than the diameter of central portion. Opening 296 is a modified keyhole opening in that the extension opening opens into an edge of the foot 294.

Blade foot 294 is dimensioned to fit within a complementary slot formed in the hinge of the cup remover to which blade 290 is attached. A pin 297 seen only in FIG. 20, retains the blade in the slot. Pin 297 has a shaft 298, a collar 302 and a head 304. Shaft 298 has a diameter less than the width of the extension of blade opening 296. Collar 302 has a diameter greater than that of shaft 298 and greater than the width of the extension of blade opening 296. Head 304 has a diameter greater than that of collar 302. Normally a spring or other biasing member holds pin to the hinge so that collar 302 seats in the central portion of blade opening 296. The seating of the pin collar 302 in the blade opening 296 releasably holds blade 290 to the rest of the acetabular cup remover. The blade is removed by moving the pin along its longitudinal axis so the pin shaft goes into registration with the center portion of blade opening 296. It is then possible to remove the blade by sliding the blade out of the hinge. During this process the section of the blade foot 294 that forms the extension of the blade opening 296 slides along the opposed sides of pin shaft 298.

A trunk 312 extends distally forward from foot 294. Trunk 312 is the portion of the blade body that is curved both along its longitudinal axis and lateral axis. In the depicted version of the invention, blade 290 is formed to have a reinforcing web 310 that extends around the corner between head 294 and trunk 312.

Blade trunk 312 has a width that varies along the length of the trunk. Specifically, along substantially most of the trunk, the width of the trunk is constant. In the depicted version of the invention this portion of the trunk has a width that is equal to the width across foot 294. Adjacent the distal end of the blade body the side surfaces of blade body flare or taper outwardly, away from the longitudinal axis along the blade. Blade body 290 has a head 318 the width of which is greater than that of the trunk 312 from which the head extends. In the depicted version of the invention, surfaces 314 are the parallel side surfaces of body trunk 312. Surfaces 316 are the outwardly flared side surfaces. In the depicted version of the invention the blade is formed so that each surface 316 is concave in shape. Surfaces 320 are the distalmost side surfaces of the blade. Surfaces 320 are parallel.

Blade 290 is formed to have teeth 324a-324p. Each tooth has a rake surface and a clearance surface that meet to form a cutting edge. Parallel side surfaces 320 form the rake surfaces of outermost teeth, teeth 324a and 324p. Generally teeth 324a-324p are similar to teeth 214a-214j of blade 210. On at least one surface of the blade, at least one tooth is formed with a groove 326 that extends proximally from the clearance surface along the blade body. In the depicted version of the invention, blade 290 is formed so that a groove 326 extends inwardly from the outwardly facing surfaces of teeth 324c, 324e, 324g, 324j, 324l and 324n. While not illustrated, blade 290 may be further formed so that grooves extend inwardly from the inwardly facing surfaces of at least some of the teeth.

Blade 290 includes more teeth than the previously discussed versions of the invention. This means that per each sweep of the blade more bone/cement can be sheared away from the space adjacent the cup 34 against which the blade is applied. Blade 290 has these additional teeth even though the width of the proximal portion of the blade, foot 294 is not larger than the width of the above discussed blades. Thus blade 290 can offer increased cutting efficiency without requiring that the blade be used with an acetabular cup remover that is especially dimensioned to accommodate the blade.

Figure 23:
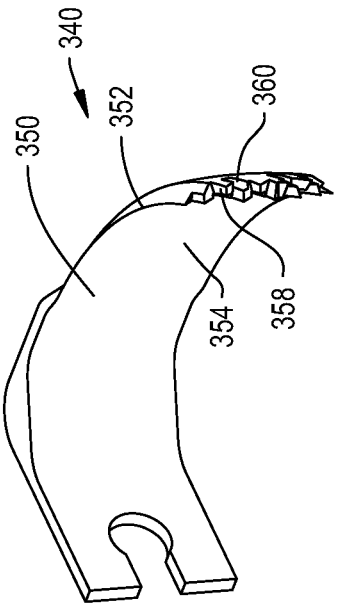
FIG. 23 is an alternative perspective view of the blade of FIG. 22.
Figure 22:
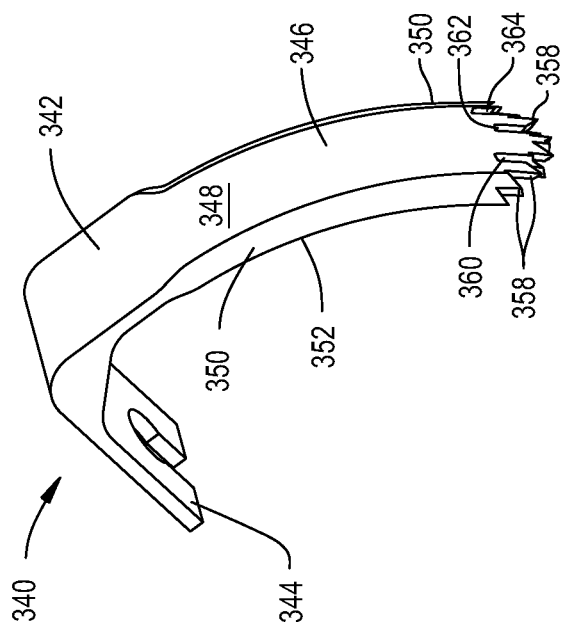
FIG. 22 is a perspective view of the outer surface of a sixth blade of this invention.

FIGS. 22 and 23 depict a sixth blade, blade 340, of this invention. Blade 340 includes a blade body 342. Blade body 342 includes a foot 344 essentially identical to foot 294 of blade 290.

Blade body 342 includes a trunk 346 that extends distally forward of foot 344. Trunk 346 is formed to have opposed outer and inner surfaces, surfaces 348 and 354, respectively. Approximately 2 to 20 mm forward of foot 344, the trunk is formed so that the width across outwardly directed surface 348 is approximately 1 to 10 mm less than the width inwardly directed surface 354. Opposed tapered side surfaces 350 from the end of each outer surface to the adjacent end of the inwardly directed surface. Each side surface 350 and adjacent inwardly directed surface 354 meet to define a side edge 352. The opposed side edges 352 (only one shown in both FIGS. 22 and 23) extend arcuately along the trunk of the blade body.

Blade 340 is depicted as having teeth 358 with grooves 360, 362 and 364. Teeth 358 are analogues to teeth 214. Grooves 360, 362 and 364 are analogues to grooves 230, 232 and 234.

Blade 340 is used in a manner similar to the previously described blades. A benefit of blade 340 is that when the blade is oscillated, side edges 352 cut soft tissue that is located near the blade. This tissue includes fibrous tissue that may have formed around the cup to be removed.

FIG. 24 depicts the distal end of an additional blade 370 of this invention. Blade 370 has a blade body 372. Blade 370 is formed with teeth 374a-374p. Each tooth has a rake surface 376 and a clearance surface 382 (two each surfaces identified). Each tooth rake surface 376 and clearance surface 382 meets at the cutting edge 380 of the tooth. In this version of the invention teeth 374b-374d and 374m-374o have positive rake angles. Thus, the rake surfaces of these teeth appear to extend outwardly, away from the longitudinal axis of the blade 370. Teeth 374a, 374e-374l and 374p have 0°, neutral rake angles.

In this version of the invention, teeth 374b-374d and 374m-374o even though directed away from the laterally directed, do not chisel the bone or cement to which they are applied. Instead, the bone/cement is, as described above, is removed by the more efficient shearing action.

It should further be understood that all of teeth 374a-374p of blade 370, like the teeth of the other described versions of the invention, are further formed so that the clearance surfaces 382 of the teeth do not project distally forward of the rake surfaces of the teeth with which they are associated.

The above is directed to specific versions of the invention. Alternative versions of the invention may have features different from what has been described. For example. The number of teeth the blades of this invention are shown to have is understood to be exemplary, not limiting.

Further the features of the blades may be interchanged. Thus, there may be some versions of the invention wherein the blade have teeth with rake surfaces that are tapered and that are further formed to have grooves similar to grooves 230-240 or grooves 270-280. Also there may be some versions of the invention wherein the grooves formed in the teeth have different widths. Thus, it may be desirable to provide one or more teeth with narrow width proximally extending grooves. This would be useful if it was desirable to provide some of the teeth with grooves with cutting edges that extend the full width of the blade. Still other teeth on the same blade would be formed with longer width grooves. Thus, these teeth may have cutting edges that are relatively short in length, being truncated by the presence of the grooves. However, the grooves integral with these teeth, being large in cross sectional area, are able to receive and direct a relatively large volume of the debris away from the distal end of the blade in which they are formed.

Likewise, some blades of this invention may be designed such that some, but not all of the teeth have the tapers, the shear, of the teeth of blade 180. In some preferred versions of this embodiment of the invention, less than all of the teeth are provided with a shear or taper and the teeth that are provided with a shear are formed so as to have rake surfaces that extending from the outer surface to the inner surface are on planes that extend away from the plane that intersects the center of the reference sphere, the longitudinal center plane of the blade body. These would be rake surfaces 198c, 198e, 198g and 198i of the blade of FIG. 11. Providing the teeth with these rake surfaces facilitates the pushing of the debris cut in the cup removal process away from the cup and blade.

In still other embodiments of the invention, teeth are provided with a shear and the teeth that are provided with a shear formed so as to have rake surfaces that extending from the inner surface to the outer surface are on planes that extend toward the plane that intersects the center of the reference sphere, the longitudinal center plane of the blade body. These would be rake surfaces 198b, 198d, 198f and 198h of the blade of FIG. 11.

Likewise, in some versions of the invention, plural adjacent teeth may have the shear of tooth 190b. In some versions of the invention plural adjacent teeth may have the shear of tooth 190c. In some versions of the invention a tooth with the shear of tooth 190b or the shear of tooth 190c may be adjacent a tooth that is without any shear or taper (the axis that extends between the opposed outer and inner surfaces of the tooth is parallel to the longitudinal center plane of the blade body. Thus, there is no requirement that in all versions of the invention, a tooth with an axis along the rake surface that, extending from the outer surface of the tooth to the inner surface of the tooth, that extends towards the longitudinal center plane always be adjacent a tooth with an axis that is directed in the opposite direction.

Further, it should be understood that the arcuate length of the blade body may vary from what has been shown. It is believed that many cup removers 30 of this invention may use plural blade in a single procedure. A first blade that subtends an arc of between 10° and 45° may be employed to initially form a shallow cut or kerf around the acetabular cup 34. Once this cut is formed a blade that subtends an arc of at least 45° and typically no more than 90° may be fitted to the cup remover. This blade is used to form a final cut. Often this cut does not extend around the distal end tip of the cup 34. This leaves a small stem between the cup and underlying bone that that is relatively easy to break in order to remove the cup from the hip in which the cup is fitted. In some procedures the cut formed by the acetabular cup remover of this invention does completely separate the cup from the underlying bone.

In the described versions of the invention, the blade teeth appear to extend proximally rearward from the center of the blade on lines that extend outwardly from the center. In alternative versions of the invention, the teeth, or at least a portion of the teeth may be located on an arc. The center of this arc would typically be a point intersected by an extension of the longitudinal axis through the blade.

Also, in the described versions of the invention the rake surfaces of the outer teeth of each blade generally are parallel to, extensions of, the side surfaces of the blade body. This is exemplary, not limiting. In alternative constructions of this invention, these rake surfaces may lie on planes that are not contiguous with the side surfaces. For example, a version of blade 44 may be provided with teeth 150*a* and 150*n* that have rake surfaces in planes similar in orientation to the rake surface of adjacent teeth 150*b* and 150*m*, respectively.

In the above described versions of the invention, the teeth have a 0° rake angle. This is not limiting the scope of this invention. In alternative versions of the invention, the teeth may have a positive rake angle and, in some instances a negative rake angle. For example, an alternative version of blade 44 may have teeth with rake surfaces that are on planes different from what is described above. In these versions of the invention, if the teeth have positive rake angles each rake surface may be located on a plane one axis of which extends from the virtual center of the acetabular cup against which the blade is to be applied. The second plane-defining axis is along a line that which converges with the extension of the longitudinal axis through the blade. In versions of the invention constructed so that the teeth have positive rake angle, the points at which these axis-defining lines and the extension of blade longitudinal axis meet are located forward of the distal end of the blade.

Similarly, in some of the depicted versions of the blades of this invention with grooves, dubs or channels are depicted as having three grooves on each side of the blade. This is only for purposes of illustration. Other versions of this invention in which the blade is provided with grooves may have less than or more than three grooves on each side of the blade. Likewise, there is no requirement that the opposed inner and outer surfaces of the blade with groove have the same number of grooves on each surface. Also, there is no requirement that in all versions of the invention, the depth of each groove consistently decrease along the length of the groove as the groove extends proximally from the distal end of the blade. In some versions of the invention the depth of one or more of the grooves may be substantially constant along the length of the groove.

In versions of the invention in which the blade is formed with grooves, there is no requirement that each groove be centered on a longitudinal axis that is parallel to the longitudinal axis of the blade in which the groove is formed. In some versions of the invention two or more of the grooves may angled inwardly, towards the longitudinal axis. These grooves may meet at a depression formed in the blade that is spaced from the distal end of the blade. This depression functions as a catchment for holding the debris formed as a result of the cutting process. Likewise, one or more of the grooves may as they extend proximally extends outwardly, away from the blade longitudinal axis. These grooves may even extend to the sides of the blade. These grooves thus function as conduits through which the debris are forced to flow away from the blade. A blade of this invention may even have grooves that extend in different directions. For example, the inner located grooves may extend to a depression. The grooves located adjacent the sides of the blade may extend to the sides.

Likewise the blade features that releasably hold the blade to the rest of the cup remover 30 may vary from what has been described.

Figure 25A:
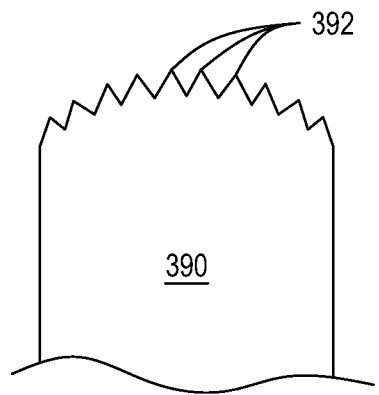
FIGS. 25A-25C depict alternative tooth patterns of the blade of this invention.
Figure 25B:
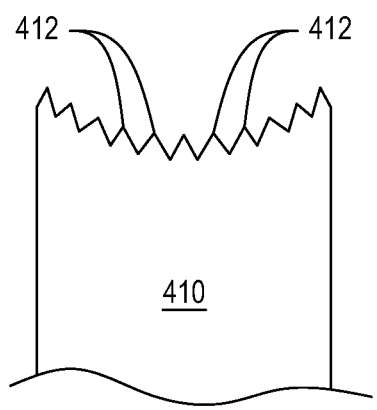

The blades of this invention described in detail are constructed so that the teeth located adjacent the longitudinal axis of the blade are the most distal of the teeth. This is understood to only be illustrating, not limiting. In some versions of the invention the teeth 392 may be arranged in a wave pattern across the width of the blade as seen in FIG. 25A. In still other versions of the invention the teeth may be arranged so that the most proximal tooth is actually located adjacent the longitudinal axis of the blade. As seen with respect to blade 410 of FIG. 25B, on either side of the longitudinal axis, each tooth 412 is located forward of the adjacent tooth located closer to the longitudinal axis. Thus, the outermost teeth of the blade, the teeth located furthest from the longitudinal axis are both essential the two distal-most located teeth of the blade.

Figure 25C:
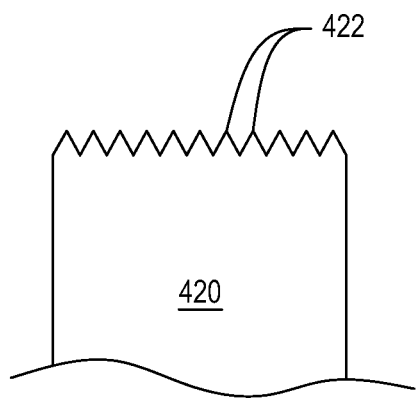

Further, the teeth may be arranged in line that extends perpendicularly relative to the longitudinal axis of the blade 420 as seen in FIG. 25C. Here the opposed faces of each tooth 422 function as opposed rake surfaces that define a cutting edge. In FIG. 25C the teeth 422 are shown as all having a positive rake angle. This is not limiting. A blade of this invention can be provided wherein the teeth have neutral or negative angles.

Also, the actual structure of the acetabular cup remover is understood to be exemplary not limiting. Some powered acetabular cup removers of this invention may not have the assembly that indexes, rotates, the blade around the driver that oscillates the blade. Still other acetabular cup removers of this invention may be manually operated. These cup removers may be designed so that the blade is fixedly attached to the rest of the cup remover. Then, in order to apply the blade against the cup to which the remover is applied, the remover is tilted. This tilting angles the blade forward over the cup.

Similarly it should be understood that in some versions of the invention the blade is shaped so that while both the longitudinal and lateral axes of the blade body are curved, the curves do not share a common radius. This is because some acetabular cups themselves are not purely spherical in shape. Blades therefore with radii that vary can facilitate the removal of these cups.

In still other embodiments of the invention, the rake faces and the clearance faces may not be a perfect plane, instead having a concave or convex curvature. The rakes surfaces are still substantially defined by two axes. The first axis of each of these planes is an axis parallel to the longitudinal axis of the blade body. The second axis of each of these planes intersects the first axis and also intersects the center of the sphere defined by the acetabular cup 34 against which blade 44 is to be applied.

Further while this invention is described as a cup remover and blade for removing an acetabular cup 34, the components of this invention may have utility beyond this primary described utility. Accordingly, the blade of this invention may be used with surgical instruments other than acetabular cup removers.

In versions of the invention wherein the head of the blade body is wider than the proximal portion, the trunk, of the blade body, the transition surfaces may not always be concave ad depicted in FIG. 27. These surfaces could be convex, have a linear taper or be a combination of straight and curved.

It is therefore an object of the appended claims to cover all such variations and modifications as come within the true spirit and scope of this invention.

What is claimed is:

1. A blade for use with an acetabular cup remover, said blade including:
    a body, said body having: opposed inner and outer surfaces, the inner surface being directed towards the acetabular cup against which the blade is placed; proximal and distal ends; sides that extend between the ends; a longitudinal axis that extends between the proximal and distal ends; a longitudinal center plane that extends through the longitudinal axis; and a lateral axis that extends between the sides and, wherein, said body is at least partially curved so that, at least adjacent the distal end of said blade body, both the longitudinal axis and the lateral axis of said blade body are curved;
    a coupling feature attached to the proximal end of the body that cooperates with a complementary coupling feature of the acetabular cup remover so as to removably hold the blade to the acetabular cup remover; and
    teeth that project forward from the distal end of the blade body, each said tooth having: an outer surface adjacent the blade body outer surface; an inner surface adjacent the blade body inner surface; a rake surface; a clearance surface and a cutting edge, wherein at least a plurality of said teeth are further defined so that the rake surfaces and the clearance surfaces of the teeth meet to define the cutting edges of said teeth and wherein, on each side of the longitudinal center plane of the blade body, there is:
        an outer tooth spaced furthest from the longitudinal center plane; and
        a plurality of inner teeth spaced closer to the longitudinal center plane, the plurality of inner teeth including: at least one inner tooth that has a rake surface that is located on an axis that, extending from the outer surface of the tooth to the inner surface of the tooth, extends away from the longitudinal center plane and at least one inner tooth that has a rake surface that is located on axis that, extending from the outer surface of the tooth to the inner surface of the tooth, extends towards the longitudinal center plane.

2. The blade of claim 1, wherein said inner teeth on opposed sides of the longitudinal center plane of said blade body are collectively are arranged so that: there is a first plurality of inner teeth that each have a rake surface that is located on an axis that, extending from the outer surface of the tooth to the inner surface of the tooth, extends away from the longitudinal center plane; there is a second plurality of inner teeth that each have a rake surface that is located on an axis that, extending from the outer surface of the tooth to the inner surface of the tooth, extends towards the longitudinal center plane; and at least two of the first plurality of inner teeth alternate with at least two of the second plurality of inner teeth.

3. The blade of claim 1, wherein said coupling feature consists of a tab separate from said blade body that is attached to said blade body and that is formed with a geometric feature that cooperates with a complementary coupling feature of the acetabular cup remover so as to removably hold the blade to the acetabular cup remover.

4. The blade of claim 1, wherein: the sides of the blade body are parallel; and the outer teeth are not located outwardly of the sides of the blade body.

5. The blade of claim 1, wherein, said teeth project forward from said blade body such that said teeth adjacent opposed sides of the longitudinal center plane of said blade body are located further from the proximal end of said blade body than said teeth spaced away from the longitudinal center plane of said blade body.

6. The blade of claim 1, wherein on either side of the longitudinal center plane of said blade body said teeth are arranged so that each said tooth is located proximal to the adjacent tooth that is located closer to the longitudinal center plane.

7. The blade of claim 1, wherein said blade body is further formed so that the longitudinal and lateral axis of said blade body have a common radius of curvature.

8. The blade body of claim 1, wherein said blade body is formed so the longitudinal axis of said blade body is curved from the proximal end of said blade body to said teeth.

9. The blade of claim 1, wherein said teeth are further formed so that, on each side of the longitudinal center plane of said blade body, there are a plurality of inner teeth that each has a rake surface that is located along an axis that, extending from the outer surface of the tooth to the inner surface of the tooth, extends away for the longitudinal center plane.

10. The blade of claim 1, wherein said teeth are further formed so that, on each side of the longitudinal center plane of said blade body, there are a plurality of inner teeth that each has a rake surface that is located along an axis that, extending from the outer surface of the tooth to the inner surface of the tooth, extends towards the longitudinal center plane.

11. The blade of claim 1, wherein said teeth are further formed so that, on each side of the longitudinal axis of said blade body:
    there are a plurality of inner teeth that each has a rake surface that is located along an axis that, extending from the outer surface of the tooth to the inner surface of the tooth, extends away for the longitudinal center plane; and
    there are a plurality of inner teeth that each has a rake surface that is located along an axis that, extending from the outer surface of the tooth to the inner surface of the tooth, extends towards the longitudinal center plane.

12. A blade for use with an acetabular cup remover, said blade including:

a body, said body having: opposed inner and outer surfaces; the inner surface being directed towards the acetabular cup against which the blade is placed; proximal and distal ends;

sides that extend between the ends; a longitudinal axis that extends between the proximal and distal ends; a longitudinal center plane that extends through the longitudinal axis; and a lateral axis that extends between the sides and, wherein said body is at least partially curved so that, at least adjacent the distal end of said blade body, both the longitudinal axis and the lateral axis of said blade body are curved;

a coupling feature attached to the proximal end of the body that cooperates with a complementary coupling feature of the acetabular cup remover so as to removably hold the blade to the acetabular cup remover; and teeth that project forward from the distal end of the blade body, each said tooth having: an outer surface adjacent the blade body outer surface; an inner surface adjacent the blade body inner surface; a rake surface; a clearance surface and a cutting edge, wherein at least a plurality of teeth are further defined so that the rake surfaces and the clearance surfaces of the teeth meet to define the cutting edges of said teeth and wherein, on each side of the longitudinal center plane of said blade body, there is:

an outer tooth spaced furthest from the longitudinal center plane; and a plurality of inner teeth spaced closer to the longitudinal center plane, said plurality of inner teeth including: at least one inner tooth that has a rake surface that is located on an axis that, extending from the outer surface of the tooth to the inner surface of the tooth, extends away from the longitudinal center plane and, adjacent that said inner tooth, an inner tooth that has a rake surface that is located on axis that, extending from the outer surface of the tooth to the inner surface of the tooth, extends towards the longitudinal center plane.

13. The blade of claim 12, wherein said inner teeth on opposed sides of the longitudinal center plane of said blade body are collectively are arranged so that: there is a first plurality of inner teeth that each have a rake surface that is located on an axis that, extending from the outer surface of the tooth to the inner surface of the tooth, extends away from the longitudinal center plane; there is a second plurality of inner teeth that have each a rake surface that is located on an axis that, extending from the outer surface of the tooth to the inner surface of the tooth, extends towards the longitudinal center plane; and at least two of the first plurality of inner teeth alternate with at least two of the second plurality of inner teeth.

14. The blade of claim 12, wherein said coupling feature consists of a tab separate from said blade body that is attached to said blade body and that is formed with a geometric feature that cooperates with a complementary coupling feature of the acetabular cup remover so as to removably hold the blade to the acetabular cup remover.

15. The blade of claim 12, wherein: the sides of the blade body are parallel; and the outer teeth are not located outwardly of the sides of the blade body.

16. The blade of claim 12, wherein, said teeth project forward from said blade body such that the teeth adjacent opposed sides of the longitudinal center plane of said blade body are located further from the proximal end of the blade body than said teeth spaced away from the longitudinal center place of said blade body.

17. The blade of claim 12, wherein on either side of the longitudinal center plane of said blade body said teeth are arranged so that each said tooth is located proximal to the adjacent tooth that is located closer to the longitudinal center plane.

18. The blade of claim 12, wherein said blade body is further formed so that the longitudinal and lateral axis of said blade body have a common radius of curvature.

19. The blade of claim 12, wherein said blade body is formed so the longitudinal axis of said blade body is curved from the proximal end of said blade body to said teeth.

20. The blade of claim 12, wherein said teeth are further formed so that, on each side of the longitudinal axis of said blade body:

there are a plurality of inner teeth that each has a rake surface that is located along an axis that, extending from the outer surface of the tooth to the inner surface of the tooth, extends away for the longitudinal center plane; and there are a plurality of inner teeth that each has a rake surface that is located along an axis that, extending from the outer surface of the tooth to the inner surface of the tooth, extends towards the longitudinal center plane.

* * * * *